(12) United States Patent
Reeve

(10) Patent No.: US 10,500,068 B2
(45) Date of Patent: Dec. 10, 2019

(54) MEASURING INSTRUMENT FOR USE IN ORTHOPAEDIC SURGERY

(71) Applicant: DEPUY IRELAND UNLIMITED COMPANY, Cork (IE)

(72) Inventor: Michael Reeve, Leeds (GB)

(73) Assignee: DEPUY IRELAND LIMITED COMPANY, Loughbeg Industrial Estate, Cork (IE)

( * ) Notice: Subject to any disclaimer, the term of this patent is extended or adjusted under 35 U.S.C. 154(b) by 330 days.

(21) Appl. No.: 15/651,205

(22) Filed: Jul. 17, 2017

(65) Prior Publication Data

US 2017/0333220 A1    Nov. 23, 2017

Related U.S. Application Data

(63) Continuation of application No. 14/407,208, filed as application No. PCT/GB2013/051367 on May 24, 2013, now abandoned.

(30) Foreign Application Priority Data

Jul. 4, 2012  (GB) .................................. 1211886.5
Jan. 31, 2013  (GB) .................................. 1301741.3

(51) Int. Cl.
*A61F 2/46*  (2006.01)
*A61B 17/02*  (2006.01)

(52) U.S. Cl.
CPC .......... *A61F 2/4657* (2013.01); *A61F 2/4684* (2013.01); *A61B 2017/0268* (2013.01); *A61F 2002/4658* (2013.01)

(58) Field of Classification Search
CPC ....................... A61F 2002/4658; A61F 2/4657
See application file for complete search history.

(56) References Cited

U.S. PATENT DOCUMENTS

| | | |
|---|---|---|
| 2,325,558 A | 7/1943 | Uslan |
| 2,936,526 A | 5/1960 | Dupre |
| 5,486,178 A | 1/1996 | Hodge |
| 5,700,268 A | 12/1997 | Bertin |
| 6,056,756 A | 5/2000 | Eng |
| 7,261,719 B1 | 8/2007 | Twomey |
| 7,275,336 B2 | 10/2007 | Casutt et al. |

(Continued)

FOREIGN PATENT DOCUMENTS

WO    WO-2011141723 A1 * 11/2011 ........... A61B 17/155

OTHER PUBLICATIONS

Australian Search Report for Corresponding Australian App. No. 20170251689 dated Jan. 15, 2019 (Jan. 15, 2019), 15 Pages.

(Continued)

*Primary Examiner* — Samuel S Hanna

(57) ABSTRACT

A measuring instrument (2) for use during an orthopaedic surgical procedure to measure first and second distances from a reference point on a bone to first and second measurement points respectively. The measuring instrument has a first scale (24) for displaying the first distance and a second scale (28) for displaying the second distance. It includes a mask (26) which can be positioned against the second scale after the first distance has been measured in a position that is selected relative to the second scale dependent on the measured first distance, to restrict the length of the second scale that is visible to the user.

7 Claims, 5 Drawing Sheets

(56) References Cited

U.S. PATENT DOCUMENTS

| | | |
|---|---|---|
| 7,488,324 B1 | 2/2009 | Metzger |
| 8,828,020 B2 | 9/2014 | Dower |
| 9,113,913 B2 | 8/2015 | Reeve |
| 2003/0093080 A1 | 5/2003 | Brown et al. |
| 2004/0097951 A1 | 5/2004 | Steffensmeier |
| 2005/0059980 A1 | 3/2005 | Overes |
| 2006/0217737 A1 | 9/2006 | Iversen |
| 2007/0162036 A1 | 7/2007 | Schifrine |
| 2009/0076519 A1 | 3/2009 | Iversen |
| 2009/0326544 A1 | 12/2009 | Chessar |
| 2011/0046685 A1 | 2/2011 | Faure |
| 2011/0218628 A1 | 9/2011 | Ciupik et al. |
| 2013/0144302 A1 | 6/2013 | Reeve |
| 2014/0148811 A1 | 5/2014 | Reeve |

OTHER PUBLICATIONS

PCT International Search Report for International App. No. PCT/GB2013/051367 dated Jul. 12, 2013 (Jul. 12, 2013), 11 Pages.
GB Search Report for GB Application No. GB1211886.5 dated Oct. 30, 2012 (Oct. 30, 2012), 4 Pages.
Chinese Search Report for Corresponding Chinese Application No. 201380035869.3, dated Oct. 16, 2015 (Oct. 16, 2015), 3 Pages.

\* cited by examiner

MEASURING INSTRUMENT FOR USE IN ORTHOPAEDIC SURGERY

CROSS REFERENCE TO RELATED APPLICATION

This application is a continuation of U.S. patent application Ser. No. 14/407,208, filed Dec. 11, 2014, which is a National Stage 35 U.S.C. 371 of International Patent Application PCT/GB2013/051367 filed May 24, 2013, which claims priority to United Kingdom Application No. 1211886.5, filed Jul. 4, 2012 (now abandoned) and which claims priority to United Kingdom Application No. 1301741.3 filed Jan. 31, 2013, all of which are incorporated by reference in their entireties.

BACKGROUND OF THE INVENTION

This invention relates to a measuring instrument for use in orthopaedic surgery.

It is important for the success of a surgical procedure to replace an orthopaedic joint to determine as accurately as possible the configuration of the patient's natural joint. This information facilitates the correct selection of the components of a joint prosthesis for use during the procedure, and the correct positioning of the prosthesis components during the procedure. Correct selection and positioning of the prosthesis components can help to ensure that the joint provides the desired biomechanical performance after implantation.

Accurate determination of the configuration of a patient's joint is particularly important in relation to the implantation of a knee joint prosthesis. For example, it can be important to determine (a) the size of the femur measured along the anterior-posterior axis, (b) the proximal extent of the femoral sulcus, and (c) the distance between the femur and the proximal tibia, and the rotational orientation of the tibia relative to the femur, when the joint soft tissue is appropriately tensioned. These factors can determine the selection of components which are to be implanted in the knee replacement procedure, including the size of the femoral component and the size of the spacer which is to be provided between femoral component and the tibial component. The factors can be inter-related in that, for example, a change in the size of the femoral component that is selected will affect the distance between that component and the proximal face of the tibial component. This will have an effect on the tension in the joint soft tissue for a particular size of bearing or spacer component.

It is known to select the size of the femoral component of a knee joint prosthesis by measuring the distance from the posterior condylar surface to the anterior condylar surface. This measurement can be performed before the start of the joint replacement procedure using images of the femur. However, it is generally desirable to measure this distance during the procedure. This can be done through the incision which is made to access the joint by placing the knee in flexion.

The size of the bearing spacer component which is used between the femoral component and the tibial component can also be selected before the start of the joint replacement procedure using images of the joint. Again, it is generally desirable to obtain additional distance data during the procedure. Measurements can be made with the knee in flexion. Additional measurements can be made with the knee in extension. The measurements of the distance between the femur and the tibia requires that the soft tissue extending between the femur and the tibia is placed in tension.

A preferred approach to measuring the femur in a knee replacement procedure makes use of a sizing guide which has a pair of feet which contact the posterior condyles, and a stylus which contacts the anterior cortex, extending beyond the femoral sulcus. The position of the stylus can be adjusted to adjust the point along the length of the anterior cortex at which the anterior cortex is contacted by the stylus. Such a sizing guide is disclosed in WO-A-2011/141722.

US-A-2007/162036 discloses a device which can be used to determine the size of a femoral component and the size of a bearing component for use in knee replacement procedure. The device is located on a rod which is inserted into the intramedullary canal of the patient's femur. The size of the femoral component is measured in a first step by placing a pair of feet in contact with the femoral condyles while the knee is in flexion, and placing a stylus anteriorly in contact with the anterior cortex. In a subsequent step, the plate which carries the pair of feet is moved away from the posterior condyles towards the tibia to place the ligaments spanning the joint in tension. This can then be used to measure the space between the femur and the tibia. This information can be used to ensure that an appropriately sized bearing component is used in the implanted prosthesis, between the femoral and tibial components.

BRIEF SUMMARY OF THE INVENTION

The present invention provides a measuring instrument for use during an orthopaedic surgical procedure to measure first and second distances from a reference point on a bone to first and second measurement points respectively, the measuring instrument having a first scale for displaying the first distance and a second scale for displaying the second distance, the instrument including a mask which can be positioned against the second scale after the first distance has been measured in a position that is selected relative to the second scale dependent on the measured first distance, to restrict the length of the second scale that is visible to the user.

The invention also provides a measuring instrument for use during an orthopaedic surgical procedure to measure first and second distances from a reference point on a bone to first and second measurement points respectively, which comprises:

a. a reference structure which can be located relative to the reference point on the bone, b. a first measurement structure for measuring the first distance between the reference point and the first measurement point, the first measurement structure and the reference structure being capable of movement relative to one another, and the instrument including a first scale provided by a first scale portion on the reference structure and a second scale portion on the first measurement structure, the first scale indicating the position of the first measurement structure relative to the reference structure and so indicating the first distance, c. a second measurement structure for measuring the second distance between the reference point and a second measurement point, the second measurement structure and the reference structure being capable of movement relative to one another, the instrument including a second scale which is provided by a third scale portion on the second measurement structure and the first scale portion, the second scale indicating the position of the second measurement structure relative to the reference structure and so indicating the second distance, d. a mask which can be located against the first scale portion in a position that is selected according to the size of the first measurement, the mask restricting the length of at least one of the first and third scale portions that is visible.

The instrument of the invention has the advantage that the interpretation of measurement data when measuring the distance from the reference point to the second measurement point is made simpler because of the restriction on the length of the second scale that is visible to the user. This can help to reduce the incidence of errors when using the instrument.

The instrument can include a reference structure which can be located relative to reference point, and at least one measurement structure which can be moved relative to the reference structure to a position which correlates to one of the first and second measurement positions. When the instrument is for use in a knee replacement procedure to measure a patient's femur, the reference point might be the femoral anterior cortex or the posterior femoral condyles.

The reference structure can include a formation which can be positioned against the reference point to enable the reference structure to be located relative to the reference point. By way of example, when the reference point is the femoral anterior cortex, the reference structure might be a stylus which contacts the anterior cortex, extending beyond the femoral sulcus. The position of the stylus can be adjusted to adjust the point along the length of the anterior cortex at which the anterior cortex is contacted by the stylus. By way of another example, when the reference point is a posterior femoral condyle, the reference surface might be a plate or other formation which can be positioned against the posterior condyle.

The measurement structure can include a plate member having a first face which is directed towards the reference structure and a second face which is directed away from the reference structure, the first face forming part of the measurement structure. The first face can be used to position the measurement structure relative to the first measurement point and the second face can be used to position the measurement structure relative to the second measurement point. The instrument can include a driver for moving the plate member between the first and second measurement points. A plate member which is used in the instrument of the invention can be a solid plate without openings extending through it. This will be preferred for many applications. However, the plate might have one or more openings or hollows formed in it so that, in some constructions, it can be seen as for example a frame.

The instrument can include (a) a first measurement structure for measuring the first distance between the reference point and the first measurement point, the first measurement structure and the reference structure being capable of movement relative to one another, and (b) a second measurement structure for measuring the second distance between the reference point and a second measurement point, the second measurement structure and the reference structure being capable of movement relative to one another.

The first and second measurement structures can have components in common. Each of the measurement structures can include components such as a housing for mounting the measurement structure, a driver which can be operated to adjust the measurement structure, one or more scale portions. The first and second measurement structures can have any of these components (and other components) in common.

The measurement instrument can include a plate member which has a first face which is directed towards the reference structure and a second face which is directed away from the reference structure, the first face forming part of one of the first and second measurement structures and the second face forming part of the other of the first and second measurement structures. The plate member can be fixed as part of the measurement instrument (for example as a result of being formed with one or more other parts of the instrument such as by a moulding or casting technique, or by a joining technique such as welding or brazing or soldering, or by use of one or more fasteners such as screws or rivets), or it might be capable of be detached. This can facilitate use of the instrument.

The measurement instrument can include (a) a first scale provided by a first scale portion on the reference structure and a second scale portion on the measurement structure, the first scale indicating the position of the measurement structure relative to the reference structure and so indicating the first distance, and (b) a second scale which is provided by a third scale portion on the measurement structure and the first scale portion, the second scale indicating the position of the measurement structure relative to the reference structure and so indicating the second distance. The mask can be used to restrict the length of at least one of the first and third scale portions that is visible to the user. It will be apparent that the first and second scales share the first scale portion on the reference structure in this construction.

The measurement structure can include a component for fixing the measurement structure against movement relative to the bone in at least one degree of freedom. In particular, it can be preferred that the measurement structure is prevented from translating in the plane which includes the femoral anterior-posterior axis and the femoral medial-lateral axis. It can be preferred that the measurement structure can rotate at least through a limited angle about the femoral superior-inferior axis. This can enable the instrument to be aligned with both medial and lateral posterior condyles.

This can allow a measurement structure to be used to measure the first distance, and to be adjusted to measure the second distance. The measurement structure can include at least one part which is used to measure the first distance and not the second distance, and at least one part which is used to measure the second distance and not the first distance. For example, the measurement structure can include a plate member having a first face which is directed towards the reference structure and which is used to measure the first distance and a second face which is directed away from the reference structure and which is used to measure the second distance. The measurement structure can include the second scale portion which is used to measure the first distance and the third scale portion which is used to measure the second distance.

The measuring instrument can include an intramedullary rod which can be fitted in the intramedullary canal of the patient's bone. The intramedullary rod can be fixed to the measurement structure. The measurement structure can include a component by which it can be fixed to the intramedullary rod. Preferably, the rod is fitted in the intramedullary canal so that it will not move within the canal when subjected during use of the instrument to forces which might otherwise cause it to move in translation and/or rotation.

The measurement structure can include (a) a formation for locating the measurement structure relative to the first measurement point or the second measurement point, and (b) a driver for moving the formation relative to the connector component. The formation can be provided by a plate member. A plate member which is used in the instrument of the invention can be a solid plate without openings extending through it. This will be preferred for many applications. However, the plate might have one or more openings or hollows formed in it so that, in some constructions, it can be seen as for example a frame.

The formation for locating the measurement structure relative to an intramedullary rod can comprise a socket in which the end of the rod can be received. Preferably, the rod and the measurement structure can be connected to one another such that relative movement between them is prevented, at least in some degrees of freedom, for example by means of a clamp. The intramedullary rod might have a plate attached to it at its end, and the formation on the measurement structure can then enable the measurement structure to be fastened on to the plate. When the rod has a plate attached to it at its end, it will frequently be unnecessary for the measurement structure to include a socket in which the end of the rod can be received.

It can be preferred that the reference structure can be positioned on the measurement structure relative to the reference point while the measurement structure is connected against movement relative to the bone. This can be appropriate when the instrument includes a component by which the measurement structure can be fixed against movement relative to the bone in at least one degree of freedom. Accordingly, use of the instrument can involve fixing the measurement structure to the patient's bone in a position to measure one of the first and second distances, and then positioning the reference structure on the measurement structure so that it is appropriately located relative to the reference point on the bone. For example, when the reference point is on the anterior cortex on a patient's femur, the reference structure can be positioned on the measurement structure such that a stylus on the reference structure contact the anterior cortex. Preferably, the instrument includes a lock mechanism by which the reference structure can be locked against movement relative to the measurement structure.

The measurement structure can include a housing having tower portion. The reference structure can have an opening formed in it in which the tower portion of the measurement structure is received. A lock mechanism can comprise a collar on the reference structure which can be used to compress a collet against the surface of the measurement structure housing.

A driver can be used to adjust the measurement structure so that the position of a formation by which the measurement structure is located relative to a measurement point is adjusted relative to a connector for the measurement structure. A convenient driver can be based on a threaded connection between a first threaded member which is connected to the connector for the measurement structure, and a second threaded member which can mate with the first threaded member, the second threaded member being connected to the formation by which the measurement structure is located relative to a measurement point. For example, the driver can be based on a threaded connection between a threaded shaft, and a threaded bore in a rotatable knob.

The measurement structure can comprise an elongate housing. The housing can be hollow along at least part of its length. A connector for fixing the structure relative to a bone can be provided within the housing, for example in the form of a socket in which the end of an intramedullary rod can be received, or in the form of features by which the housing can be attached to a plate or other structural component on the end of a intramedullary rod. The structure can include a driver knob which is mounted on the housing along the axis of the housing so that it can rotate. The axis of rotation is parallel to or coincident with the axis of the housing. The knob has a threaded bore within it. The bore can be open at the end of the knob. This can facilitate cleaning and can mean that the length of the bore does not restrict the range of movement of the shaft within the bore. The connector can have a shaft extending from it which is threaded at one end so that the shaft can be received in the bore in the knob. When the connector is fixed to the bone, rotating the knob relative to the housing causes the shaft to translate relative to the knob. This results in translation of the measurement structure housing relative to the connector.

Preferably, at least one of the first and second scales comprises a scale portion on one component which has a single indicium and a scale portion on another component which has a plurality of spaced apart indicia. The components (the reference structure and the measurement structure) are capable of movement relative to one another. The indicium on the other component that is adjacent to the single indicium on the one component indicates the measured distance. Preferably, the single indicium that is used for the second scale in the second measurement is one of the plurality of spaced apart indicia of the first scale. For example, the first scale can be provided by (a) a first scale portion on the reference structure and (b) a second scale portion on the measurement structure that is positioned relative to the first measurement point, the first scale indicating the position of the measurement structure relative to the reference structure and so indicating the first distance between the reference point and the first measurement point. The first scale portion on the reference structure can present a plurality of spaced apart indicia and the second scale portion on the measurement structure can provide a single indicium. The first distance is indicated by the indicium on the first scale portion that is adjacent to the single indicium on the second scale portion.

The second scale can be provided by (a) a third scale portion on the measurement structure that is positioned relative to the second measurement point and (b) the first scale portion, the second scale indicating the position of the measurement structure relative to the reference structure and so indicating the second distance between the reference point and the second measurement point. The third scale portion on the measurement structure can present a plurality of spaced apart indicia and the first scale portion on the reference structure can provide a single indicium, that being the indicium on the first scale portion that was indicated in the first measurement step.

The mask can be positioned against the second scale in a position that is selected relative to the second scale dependent on the measured first distance, to restrict the length of the second scale (the first scale portion or the third scale portion or each of them) that is visible to the user. This helps the user to interpret the measurement data that is provided by the instrument. This can be particularly helpful when a common component (especially the housing of a measurement structure) provides a scale portion which is used to perform the first measurement and a different scale portion which is used to perform the second measurement. The mask can then be used to restrict the visibility of a scale portion (or a portion thereof) which is not used to perform the second measurement.

It can also be helpful when one of several indicia on a scale which is used to perform the first measurement is used as a selected indicium on a scale which is used to perform the second measurement. The mask can then be used to identify the selected indicium, restricting the visibility of other indicia on the scale which is used in the first measurement and which are not selected for use in the second measurement.

The mask can be fastened against the second scale in a plurality of different positions, each position corresponding to a different size of the first measured distance. For example, the reference structure and the mask can fit together slidingly by means of cooperating rib and groove features. For example, one of the reference structure and the mask can have one or ribs formed on it, and the other can have one or more grooves formed on it. The position of the mask on the reference structure is determined by the choice of rib and groove.

The mask can be fastened against the second scale so that it can slide relative to the second scale to allow it to be placed in a selected position corresponding to the size of the first measured distance.

The mask can be used to provide an indication to the user of the location of posterior references on the femur. For example, it can be used to provide an indication to the user of the location of the posterior cuts (through the posterior condyles) for the chosen size of femoral component of a knee joint prosthesis. Accordingly, the invention provides a kit for use in a surgical procedure which comprises:
(a) a measuring instrument according to the invention, in which the mask includes at least one posterior cut reference surface, and
(b) a femoral component of a knee joint prosthesis which includes an anteriorly facing bone contacting surface on a posterior condyle, in which the said bone contacting surface defines a posterior cut plane,
in which the posterior cut reference surface when the mask is positioned on the second scale of the instrument appropriately having regard to the measured first distance, lies in the posterior cut plane which is defined by the femoral component when the femoral component is implanted.

The invention also provides a kit for use in a surgical procedure to implant a knee joint prosthesis, which comprises:
(a) a measuring instrument according to the invention, in which the mask includes at least one posterior cut reference surface, and
(b) a femoral component trial which includes an anteriorly facing bone contacting surface on a posterior condyle, in which the said bone contacting surface defines a posterior cut plane,
in which the posterior cut reference surface when the mask is positioned on the second scale of the instrument appropriately having regard to the measured first distance, lies in the posterior cut plane which is defined by the femoral component trial when the femoral component trial is positioned on the resected femur.

Components of the instrument of the invention can be made from materials which are conventionally used in the manufacture of surgical instruments. Example of such materials include metals (for example stainless steels) and polymers (for example polyolefins such as polyethylenes and polypropylenes, polycarbonates, acetals and so on). It can be preferred that the measurement structure is made from a metal. It will frequently be preferred that the reference structure is made from a metal. The mask can be made from a polymer.

BRIEF DESCRIPTION OF THE DRAWINGS

Embodiments of the invention are described below by way of example with reference to the accompanying drawings, in which.

DETAILED DESCRIPTION OF THE INVENTION

The drawings show a measuring instrument which can be used in a surgical procedure to implant a knee joint prosthesis. Such a prosthesis comprises a femoral component which is fitted to the femur and a tibial component which is fitted to the tibia. The femoral component has a convex bearing surface which provides medial and lateral bearing surfaces corresponding to those provided by the anterior, distal and posterior surfaces of the medial and lateral condyles of the natural knee. The tibial component generally presents a flat proximal surface. A bearing component is provided between the femoral and tibial components. The bearing component has medial and lateral concave recesses on its proximal surface in which the medial and lateral condylar bearing surfaces of the femoral component can be received and can articulate. The distal surface of the bearing component is planar so that the bearing component can slide on the tibial component, in rotation or in translation or in both rotation and translation. Knee prostheses of these general types are well known.

It is common in knee replacement surgery to resect the tibia before cutting the femur. The distal cut of the femur is frequently performed after the tibial resection. The instrument that is provided by the invention can then be used to ensure that the size of the femoral component that is used is appropriate having regard to the size of the femur. It can also be used to ensure that the bearing component that is used as the appropriate thickness having regard to (a) the size of the femoral component and (b) the soft tissue which extends between the femur and the tibia.

Figure 1:
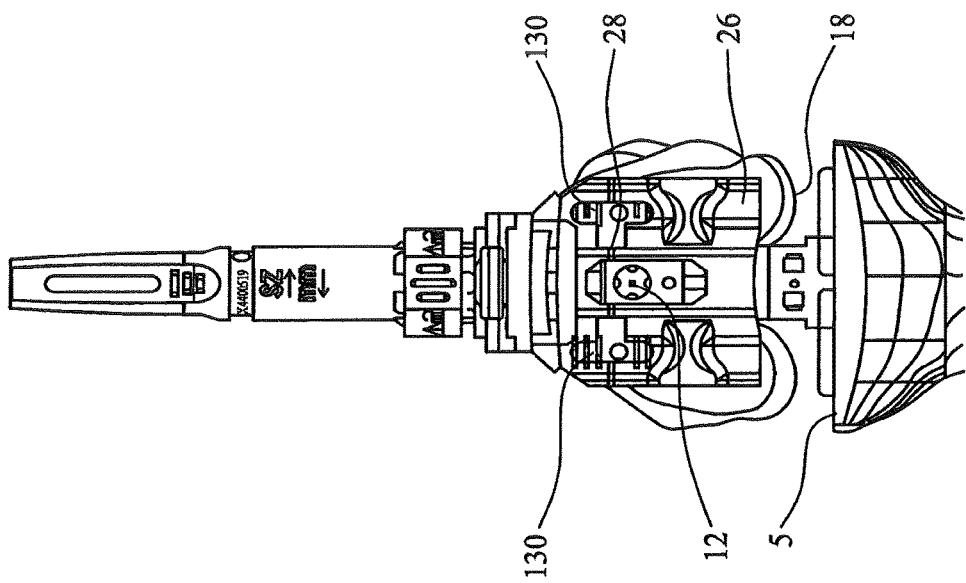
FIG. 1 is a lateral view of a measuring instrument (without its mask), shown schematically in relation to a femur and a tibia as they might be positioned in flexion during a surgical procedure to replace a knee joint.
Figure 2:
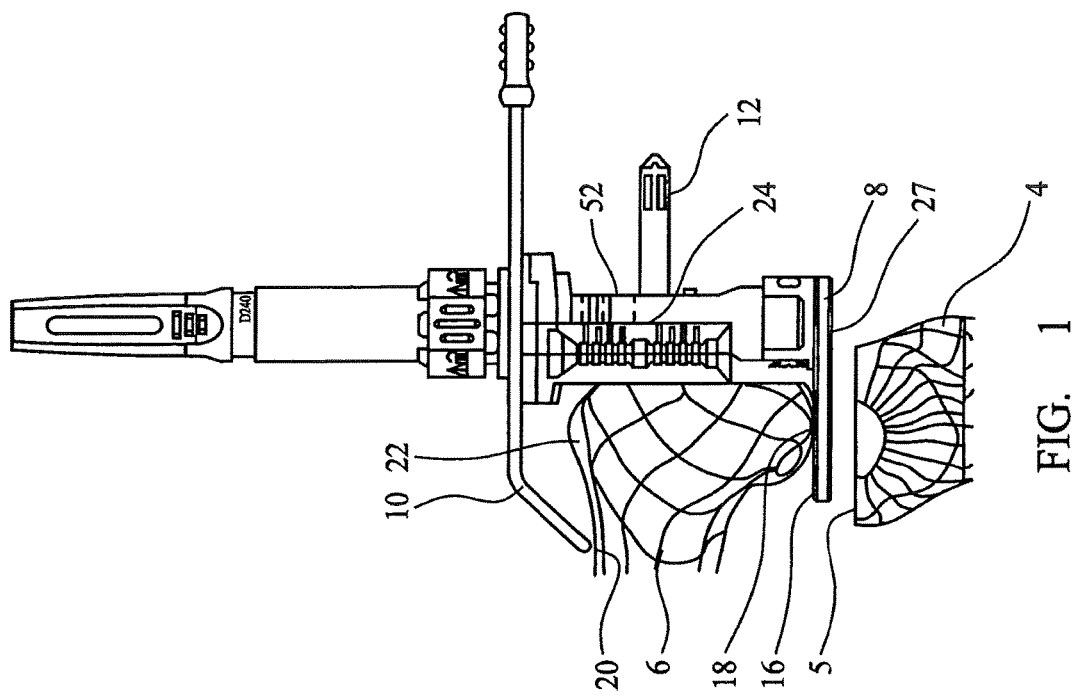
FIG. 2 is an anterior view of the measuring instrument shown in FIG. 1 (with its mask).

Referring to the drawings, FIGS. 1 and 2 show a measuring instrument 2 that is in use in a surgical procedure to implant a knee joint prosthesis, illustrating the way in which the instrument is used in such a procedure. The drawings show the tibia 4 which has been resected proximally to define a flat surface 5 on to which the tibial component (not shown) of the prosthesis can be implanted, and the femur 6 which has been resected distally.

The instrument has a plate member 8 and a stylus 10. The instrument is mounted on an intramedullary rod 12 which is located in the intramedullary cavity in the femur. The instrument allows the position of the plate member 8 to be moved relative to the intramedullary rod 12 until the upper face 16 of the plate member is in contact with the femoral posterior condyles 18. The instrument is shown in this configuration in FIG. 1. As discussed below, the location of the tip of the stylus can be adjusted relative to the reference portion (on which it is mounted) along the superior-inferior axis, and the location of the reference portion (with the stylus) can be adjusted relative to other component of the instrument along the anterior-posterior axis. These adjustments allow the position of the stylus 10 to be adjusted until the tip of the stylus is in contact with the anterior cortex 20, beyond the femoral sulcus 22.

Figure 6:
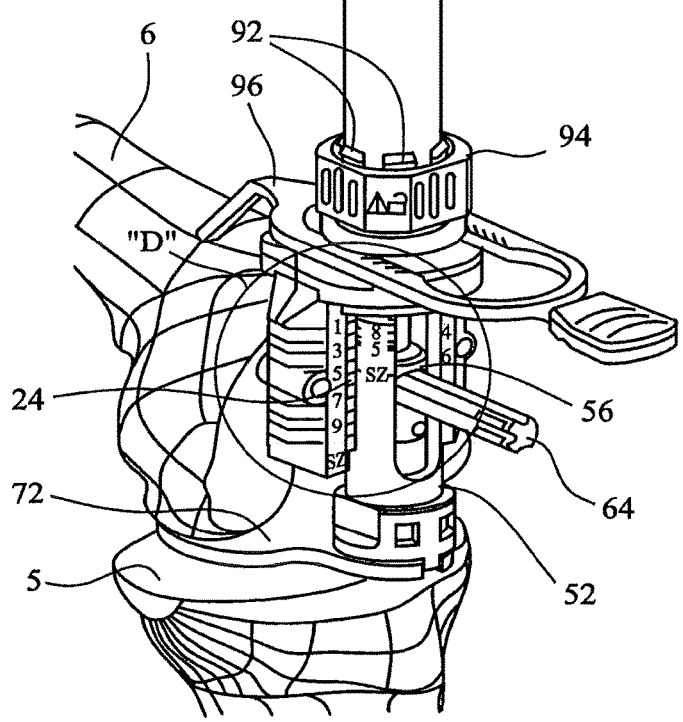
FIG. 6 is an isometric view of the instrument when the plate member in contact with the femoral posterior condyles.

The instrument provides a first scale 24 (see FIGS. 4 and 6) from which information relating to the distance between the posterior condyles and the anterior cortex, measured in a direction parallel to the anterior-posterior axis, can be obtained. As discussed below, this is provided by locating a single indicium 104 on the measurement structure against a set 108 of indicia on the reference structure, where the set of indicia provides a first scale portion and the single indicium provides a second scale portion.

The position of the plate member 8 can be moved relative to the intramedullary rod 12 until the lower face 27 of the plate member is in contact with the flat face 5 of the resected tibia. The movement of the plate member can result in the soft tissue which extends between the tibia and the femur to be placed under tension. The instrument is shown in this configuration in FIG. 2.

Figure 7:
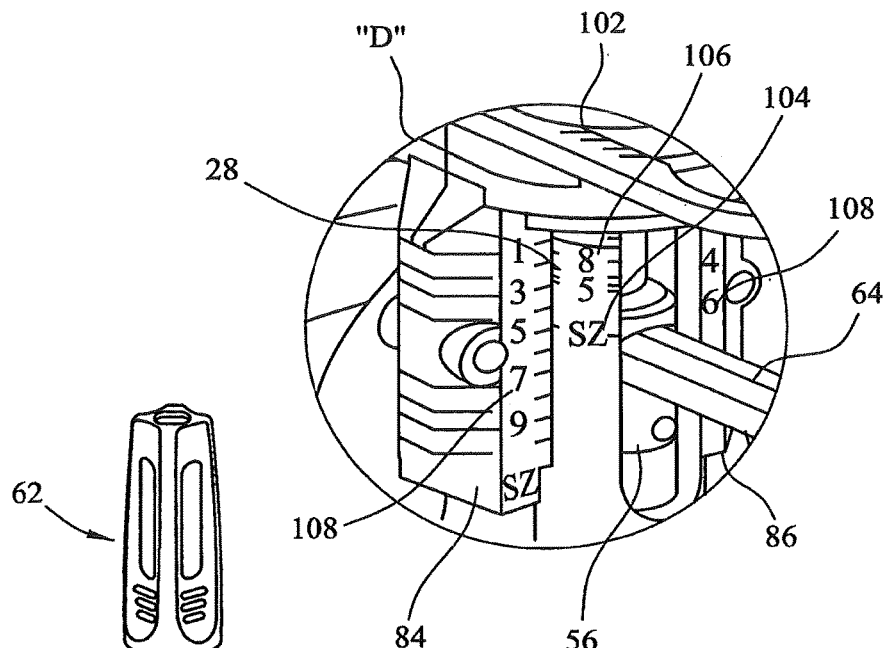
FIG. 7 is an enlarged view of the first scale on the instrument as shown in FIG. 6.

FIG. 2 shows the instrument shown in FIG. 1 with its mask 26 attached. The mask provides a window 132 through which a limited length of a second scale 28 (see FIG. 7) on the instrument is visible, which provides information relating to the distance between the anterior cortex and the flat face of the resected tibia, measured in a direction parallel to the anterior-posterior axis, can be obtained. This information can be used to select a bearing component having an appropriate thickness having regard to the size of the femoral component, and the soft tissue which extends between the femur and the tibia.

Figure 3:
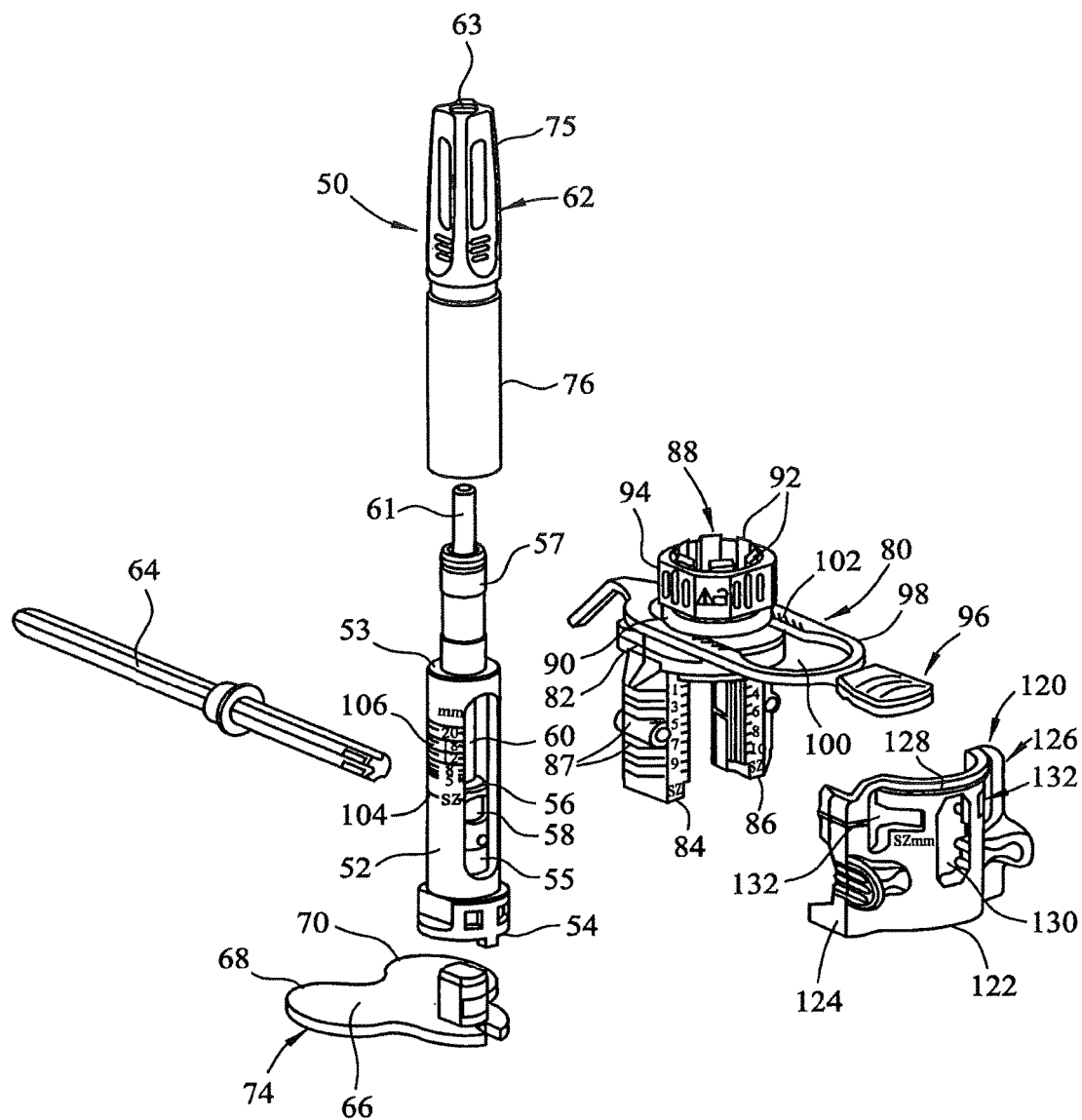
FIG. 3 is an exploded view showing separated components of the instrument shown in FIGS. 1 and 2.

FIG. 3 shows separate components of the instrument. A measurement structure 50 comprises a hollow elongate housing 52 which is hollow and has a circular cross-section when viewed along its length. The housing has upper and lower ends 53, 54. A pair of slots are formed in the housing wall. The front slot 55 is visible in FIG. 3. A turret portion 57 extends from the upper end 53 of the housing 52.

The hollow housing contains a connector block 56 which has a transverse bore 58 extending through it. A shaft 60 extends through the housing 52 and through the turret 57 along the housing axis from the connector block towards the upper end 53 of the housing. The shaft is threaded at the end 61 which is remote from the connector block.

The measurement structure includes a driver assembly 62 which is mounted on the upper end 53 of the housing 52. The driver assembly includes a driver knob 75 and a driver sleeve 76. The driver sleeve fits over the turret on the housing so that the lower end of the driver sleeve sits on the upper end of the housing. The turret is a close fit within the driver sleeve so that the driver sleeve and the driver knob can rotate on the turret relative to the housing. The driver knob has a threaded bore 63 within it, the thread in the bore of the knob 62 cooperating with the thread on the end 61 shaft 60 so that, when the driver knob and the driver sleeve are rotated relative to the housing and turret, the shaft is cause to move within the housing and the turret along the housing axis. The bore can be open at the top end of the knob. This can facilitate cleaning of the bore.

The measurement structure cooperates with an intramedullary rod 64 which is a sliding fit in the transverse bore 58 in the connector block 56. The intramedullary rod extends through one or both of the slots in the wall of the housing when it is received in the transverse bore in the connector block. The measurement structure can rotate around the axis which is defined by the intramedullary rod.

The measurement structure includes a plate member 66 which is fixed to the elongate housing 52 at its lower end 54 when the instrument is in use. The plate member has two lobes 68, 70 whose upper faces are shaped so as to replicate approximately the shape of the proximal face of the tibia, and which are intended to cooperate with the posterior faces of the medial and lateral femoral condyles respectively. It has upper and lower faces 72, 74 which are for contacting the posterior femoral condyles and the proximal tibia respectively.

The instrument includes a reference structure 80 which comprises a bridge portion 82 and medial and lateral limbs 84, 86. The bridge portion has a circular hole 88 extending through it which is slightly bigger than the housing 52 of the measurement structure 50 so that the reference structure can be slid on to the housing of the measurement structure.

The reference structure includes a locking collet 90 which comprises a plurality of flexible fingers 92 and a collar 94 which is threaded on to the bridge portion of the reference structure. The fingers can be deformed inwardly so as to grip the housing of the measurement structure by tightening the collar 94 down on to the bridge portion of the reference structure.

The reference structure includes a stylus 96 having a body portion 98 which has a slot 100 formed in it. The stylus is mounted on a spigot on the bridge portion of the reference structure so that it can slide relative to the bridge portion, with the spigot sliding in the slot. In this way, the effective length of the stylus can be adjusted so that it extends just beyond the sulcus to the anterior cortex. This allows the tip of the stylus to be moved along the superior-inferior axis. The stylus can include indicia 102 on the edges of the slot 100 to indicate the lengths of the different sizes of femoral component that correspond to the different positions of the stylus.

The housing 52 of the measurement structure 50 bears a single indicium 104, which is marked "SZ" in the drawings (for example see FIGS. 6 and 7) which forms part of a first scale, and a set of indicia 106 which form part of a second scale (which is discussed in more detail below). The set of indicia of the second scale is marked "mm" in the drawings (for example see FIG. 3). The reference structure 80 has a set of indicia 108 (a first scale portion) in two groups on its medial and lateral limbs respectively which cooperate with the single indicium 104 (a second scale portion) on the measurement structure to provide the first scale. The two groups of indicia on the reference structure are marked "SZ" on each of the medal and lateral limbs. The first scale is used to obtain information concerning the distance between the posterior condyles and the anterior cortex, measured in a direction parallel to the anterior-posterior axis, for use in selecting the appropriate size of a femoral component of the knee joint prosthesis. In the example shown in the drawings, the first scale indicates that the appropriate size of femoral component having regard to the measured anterior-posterior dimension is size 5.

Figure 4:
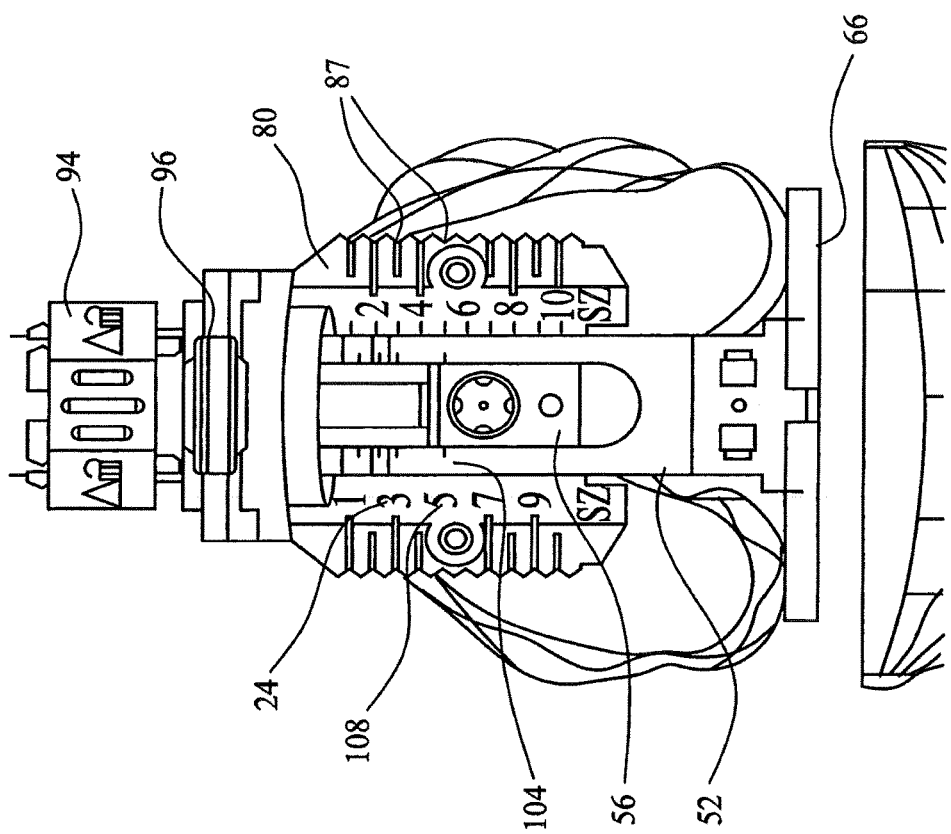
FIG. 4 is a front view of the measuring instrument shown in FIG. 1 (without its mask).

As can be seen in particular in FIG. 4, the outside edges of the medial and lateral limbs 84, 86 of the reference structure are shaped with a plurality of parallel grooves 87 extending in a direction which is parallel to the intramedullary rod 64. The spacing between the grooves can (but need not) correspond to the spacing between the indicia 108 on the reference structure.

Figure 5:
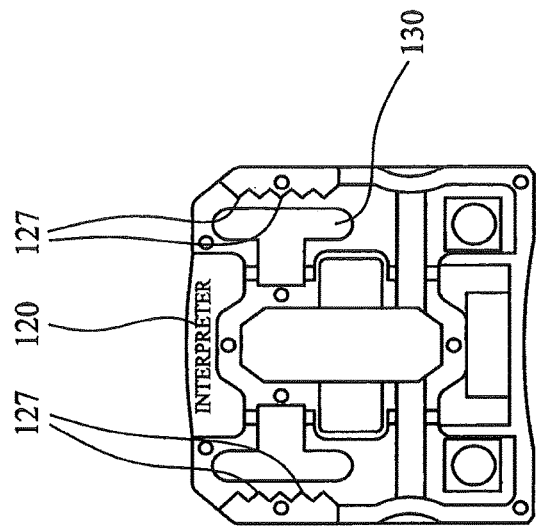
FIG. 5 is a view from behind of the mask which can be fitted to the measuring instrument shown in FIG. 4.

FIGS. 3 and 5 show the mask component 120 of the instrument. The mask has a front wall 122 and a pair of side walls 124, 126. The inside surface of each of the side walls carries a series of inwardly extending ribs 127. The spacing between the ribs corresponds to the spacing between the grooves 87 in the outside edges of the limbs of the reference structure. The ribs are a sliding fit in selected grooves of the medial and lateral limbs of the reference structure so that the side walls of the mask can be slid on to the edges of the reference structure.

Figure 9:
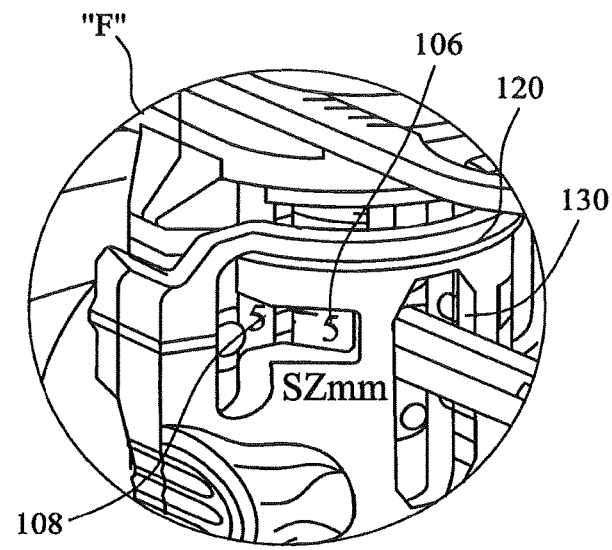
FIG. 9 is an enlarged view of the first scale on the instrument as shown in FIG. 7.
Figure 8:
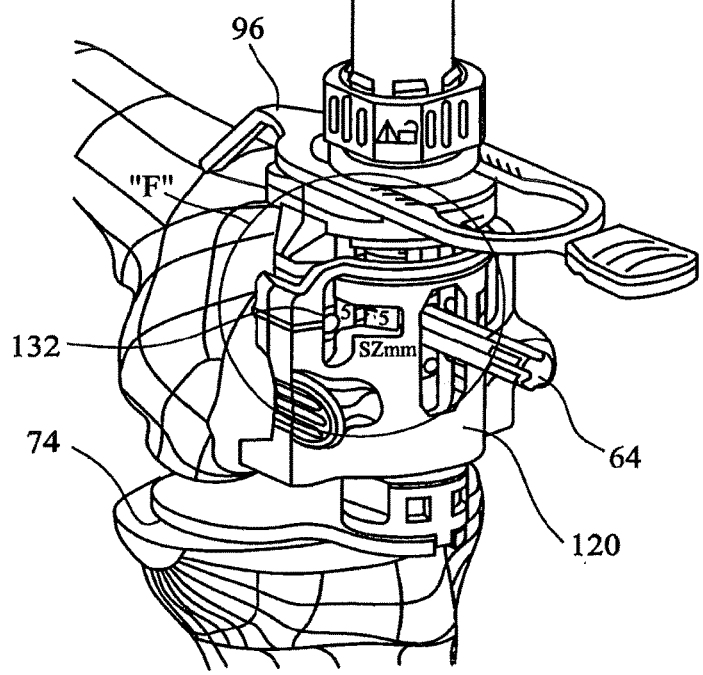
FIG. 8 is an isometric view of the instrument when the plate member in contact with the tibia.

The front wall 122 of the mask 120 is shaped to fit over the reference structure 80 and the housing 52 of the measurement structure 50 when the reference structure is fitted on to the measurement structure. Accordingly, the front wall has a central portion 128 which is arcuate. It also has a slot 130 formed in it which is aligned with the front slot 55 in the housing of the measurement structure when the mask is fitted to the reference and measurement structures, to accommodate the end portion of the intramedullary rod 64. The mask has a pair of windows 132 formed in it. The windows are generally T-shaped (with the "T" turned through 90 so that the limb of the "T" that is generally referred to as the upright limb is horizontal and the limb of the "T" that is might be referred as the cross limb is vertical). When the mask is fitted on to the assembled reference and measurement structures with the ribs on the inside surfaces of the side walls of the mask are a sliding fit in selected grooves in the outside edges of the medial and lateral limbs of the reference structure, the horizontal limb of each of the windows exposes a selected indicium from the set of indicia 108 (the first scale portion) on the reference structure, and exposes one of the indicia from the set of indicia 106 (a third scale portion) on the measurement structure 50. This can be seen in FIGS. 2 and 9, which show that the appropriate size of bearing component as 5 mm.

The instrument that is shown in the drawings has a first scale 24 which provides indicia corresponding to ten different sizes of femoral component. The distance between the anterior cortex and the posterior condyles differs between consecutive sizes of component differs by 3 mm. The distance between adjacent grooves 87 on the outside edges of the limbs of the reference structure is 3 mm.

The instrument that is shown in the drawings has a second scale which provides for bearing components to be used which have thicknesses between 5 and 22 mm. The second scale 28 indicates bearing component thickness increments of 1 mm for bearing component thicknesses from 5 to 8 mm, and bearing component thickness increments of 2 mm for bearing component thicknesses from 8 to 22 mm.

The instrument that is shown in the drawings can be used in a surgical method to replace a knee, which includes the following steps:
1. Perform the proximal tibial cut to form the planar proximal surface 5 on the tibia on which a tibial component of a knee joint prosthesis can be seated.
2. Perform the distal cut on the femur.
3. Insert the intramedullary rod 64 in the intramedullary cavity of the femur 6.
4. Locate the measurement structure 50 on the intramedullary rod 64 by positioning the end of the rod through the slots 55 in the wall of the housing 52 and through the hole 58 in the connector block 56, so that the measurement structure housing is pressed against the distal face of the resected femur.
5. Turn the knob 62 on the measurement structure (in the direction indicated by the "SZ arrow"—see FIG. 2) to draw the plate member 66 upwardly towards the femoral posterior condyles until the upper face 72 of the plate member is in contact with the posterior condyles.
6. Slide the reference structure 5480 on to the measurement structure 50 so that the measurement structure housing 52 extends through the hole 88 in the bridge portion 82 and through the collar 94, effectively moving the tip of the stylus along the anterior-posterior axis until the tip of the stylus 96 touches the femoral anterior cortex, adjusting the length of the stylus as necessary by sliding it along the anterior-posterior axis relative to the bridge portion.
7. Note the indicated size of the femoral component using the first scale provided by the single indicium 104 on the measurement structure 50 and the set 108 of indicia on the reference structure 80.
8. Fit the mask 120 to the measurement and reference structures 50, 80 by sliding the ribs on the mask into the grooves 87 on the reference structure, the grooves being selected so that the femoral component size as indicated on the scale portion on the reference structure appears towards the outward end of the horizontal limb of one of the windows 130 in the mask.
9. Turn the knob 62 on the measurement structure 50 (in the direction indicated by the "mm arrow"—see FIG. 2) to move the measurement structure including the plate member 66 downwardly towards the resected tibia until the lower face 74 of the plate member is in contacted with the tibia, and until the soft tissue extending between the tibia and the femur is placed under appropriate tension.
10. Ensure that the tip of the stylus 98 touches the femoral anterior cortex.
11. Note the size of the bearing component as indicated towards the inward end of the horizontal limb of the mask window which shows the femoral component size in towards its outward end.
12. Assess the location of the posterior cuts (through the posterior condyles) for the chosen size of femoral component of a knee joint prosthesis using the posterior edges of the mask.
13. Tighten the collar 94 on the reference structure to prevent relative sliding movement between the reference structure and the measurement structure housing.
14. Insert pins through the vertical limbs of the mask window and into the holes in medial and lateral limbs (84, 86) of reference structure to provide location for cutting block.

The invention claimed is:
1. A measuring instrument for use during an orthopaedic surgical procedure in determining the appropriate sizes of femoral and tibial implant components, the measuring instrument comprising a measurement structure, a reference structure and a mask;
    the measurement structure having a longitudinal axis, a set of indicia defining a thickness scale and a sizing indicium separate from the indicia defining the thickness scale;

the reference structure having a medial limb with an end, a lateral limb with an end and a bridge connecting the end of the medial limb and the end of the lateral limb, the bridge having a hole through which a portion of the measurement structure extends and that allows for relative sliding movement between the measurement structure and the reference structure along the longitudinal axis of the measurement structure;

at least one of the medial limb and the lateral limb including a set of indicia defining a sizing scale;

the mask including a wall portion having a window;

wherein the mask is mountable in a plurality of selective positions on the reference structure with the wall portion of the mask covering at least a portion of the thickness scale on the measurement structure and the window positioned so that one indicia on the thickness scale on the measurement structure is exposed and visible in the window while other indicia on the thickness scale on the measurement structure are covered by the wall portion of the mask.

2. The measuring instrument of claim 1 wherein one indicia on the sizing scale of the reference structure is exposed and visible in the window when the mask is mounted on the reference structure while other indicia on the sizing scale on the reference structure are covered by the wall portion of the mask.

3. The measuring instrument of claim 1 wherein the measurement structure has upper and lower ends and a housing between the upper and lower ends, the measuring instrument further comprising:

a driver assembly mounted on the upper end of the housing of the measurement structure to drive the housing in two directions of movement along the longitudinal axis; and a plate member having a first face perpendicular to the longitudinal axis of the measurement structure, the plate member being fixed to the housing of the measurement structure so that movement of the housing along the longitudinal axis by the driver assembly moves the plate member.

4. The measuring instrument of claim 3 further comprising a stylus extending outwardly from the reference structure.

5. The measuring instrument of claim 3 wherein the set of indicia defining the thickness scale and the sizing indicium are on the housing of the measurement structure.

6. The measuring instrument of claim 5 wherein the housing is hollow and has a pair of slots aligned parallel to the longitudinal axis, the measuring instrument further comprising:

a connector block having a transverse bore, the connector block being received within the housing with is transverse bore aligned with the pair of slots in the housing; and a shaft extending from the connector block through the housing along the longitudinal axis to the driver assembly.

7. The measuring instrument of claim 6 wherein the measuring instrument is part of a system that includes an intramedullary rod and wherein the intramedullary rod extends through the transverse bore of the connector block and through the pair of slots in the housing.

* * * * *